United States Patent [19]

Pressler et al.

[11] Patent Number: 5,753,471
[45] Date of Patent: May 19, 1998

[54] BIOTECHNOLOGICAL PERPARATION OF ALCOHOLS, ALDEHYDES AND CARBOXYLIC ACIDS

[75] Inventors: Uwe Pressler, Altrip; Friedhelm Balkenhohl, Limburgerhof; Bernhard Hauer; Wolfgang Ladner, both of Fussgonheim; Ursula Schnell, Bad Lippspringe; Horst Ralf Staudenmaier, Birkenheide, all of Germany

[73] Assignee: BASF Aktiengesellschaft, Ludwigshafen, Germany

[21] Appl. No.: 578,704

[22] PCT Filed: Jun. 24, 1994

[86] PCT No.: PCT/EP94/02071

§ 371 Date: Dec. 28, 1995

§ 102(e) Date: Dec. 28, 1995

[87] PCT Pub. No.: WO95/02061

PCT Pub. Date: Jan. 19, 1995

[30] Foreign Application Priority Data

Jul. 5, 1993 [DE] Germany .................. 43 22 276.5
Jul. 31, 1993 [DE] Germany .................. 43 25 850.6

[51] Int. Cl.$^6$ .................. C07C 59/60; C12P 7/22; C12P 7/24; C12N 1/20
[52] U.S. Cl. .................. 435/117; 435/118; 435/119; 435/120; 435/121; 435/122; 435/123; 435/124; 435/125; 435/126; 435/128; 435/156; 435/252.1; 435/855; 549/369; 549/374
[58] Field of Search .................. 435/117, 156, 435/122, 120, 121, 126, 128, 118, 119, 123, 252.1, 855, 124, 125; 549/369, 374

[56] References Cited

U.S. PATENT DOCUMENTS 5,213,973  5/1993  Hoeks .................. 435/117
5,217,884  6/1993  Zimmermann et al. .................. 435/117
5,236,832  8/1993  Kiener .................. 435/117

FOREIGN PATENT DOCUMENTS 442 430   8/1991  European Pat. Off. .
466042    1/1992  European Pat. Off. .
477828    4/1992  European Pat. Off. .
677791    6/1991  Switzerland .
2149783   6/1985  United Kingdom .

OTHER PUBLICATIONS

Hook G. et al., *Biochem. J.*, vol. 102, No. 2, Feb. 1967, pp. 504–510.
Ballal et al., *Biochem. and Biophys. Res. Comm.*, vol. 29, No. 3, 1967, pp. 275–280.
Raymond et al., *Appl. Microbio.*, vol. 15, No. 4, Jul. 1967, pp. 857–865.
Madhyastha et al., *Ind. J. Biochem.*, vol. 5, pp. 161–167, 1968.
Dhavalikar et al., *Ind. J. Biochem.*, vol. 3, pp. 144–157, 1966.
Shukla et al., *Ind. J. Biochem.*, vol. 5, pp. 79–91, 92–101, 1968.
Noma et al., *Phytochem.*, vol. 31, No. 8, pp. 2725–2727, 1992.
De Smet et al., *J. of Bacteriology*, vol. 171, No. 9, Sep. 1989, pp. 5155–5161, 1989.
De Frank et al., *J. of Bacteriology*, vol. 129, No. 3, Mar. 1977, pp.. 1356–1364, pp. 1365–1374.
Abraham et al., *Tetrahedron*, vol. 48, No. 32, pp. 6681–6688, 1992.

*Primary Examiner*—Herbert J. Lilling
*Attorney, Agent, or Firm*—Keil & Weinkauf

[57] ABSTRACT

A process for the biotechnological preparation of alcohols, aldehydes and carboxylic acids by oxidation of compounds of the formula $R^1$—$C(CH_3)$=$CR^2R^3$, where $R^1$, $R^2$ and $R^3$ have the meanings indicated in the description, with the aid of microorganisms is described.

8 Claims, No Drawings

BIOTECHNOLOGICAL PERPARATION OF ALCOHOLS, ALDEHYDES AND CARBOXYLIC ACIDS

The invention relates to a process for the biotechnological preparation of alcohols, aldehydes and carboxylic acids.

Highly functionalized alcohols, aldehydes and carboxylic acids are interesting products which are in demand for preparing drugs, polymers, fine chemicals etc. and which are often synthesized by oxidation of appropriate precursors.

As a rule, chemical oxidations show low regiospecificities. In addition, the reagents required for the oxidation are often toxic and/or difficult to handle.

It is known that bacteria are able in principle to oxidize methyl groups.

Thus, Raymond et al. (Appl. Microbiol. 15, (1967) 857–865) describe the oxidation of methyl groups by cooxidation with n-paraffins in the genus Nocardia.

It is known that the genus Pseudomonas oxidizes p-cymene in three steps via the alcohol and aldehyde to p-isopropylbenzoic acid (J. Bacteriol. 129, (1977) 1356–1364 and 1365–1374 and ibid 171, (1989) 5155–5161).

Besides this oxidation of benzylic methyl groups, a number of microorganisms is known to oxidize allylic methyl groups.

Thus, Noma et al. describe the oxidation of limonene by *Aspergillus cellulosae* (Phytochemistry, 31, (1992) 2725–2727) inter alia to perillyl alcohol.

*Pseudomonas incognita* oxidizes linalool inter alia to 8-hydroxylinalool (J. Bacteriol. 171, (1989) 5155–5161).

Bhattacharyya et al. have investigated in a series of studies (Indian. J. Biochem. 5, (1968) 79–91 and 92–101, Indian. J. Biochem. 3, (1966) 144–157 and Biochem. Biophys. Res. Commun. 29, No. 3, (1967) 275–279) the oxidation of terpenes (eg. limonene, α- and β-pinene) by Pseudomonas PL strains. These PL strains also oxidize p-cymene to cumic acid (Indian. J. Biochem. 5, (1968) 161–167). However, the cited studies show that, besides the required methyl group oxidations in benzylic and allylic positions, the microorganisms bring about a number of additional oxidations on the precursors used (such as limonene, p-cymene etc.).

The oxidation described in CH-B 677 791 and Tetrahedron 48, (1992) 6681–6688 of an allylic methyl group of terpenes using microorganisms of the genera Bacillus, Pseudomonas, Absidia, Rhizopus, Streptomyces, Mycobacterium, Cunninghamella, Nocardia etc. is likewise associated with the problem of side reactions.

The described reactions therefore cannot be applied industrially.

EP-A 442 430, EP-A 466 042 and EP-A 477 828 describe industrially utilizable methyl group oxidations. The disadvantage of these reactions is, however, the induction of the microorganisms by, for example, p-xylene as sole source of carbon and energy. In addition, the described reactions are restricted to 5- and 6-membered heterocycles.

Industrial processes using microorganisms which selectively oxidize both benzylic and allylic methyl group positions in a wide range of aromatic, heteroaromatic and aliphatic substances have not hitherto been disclosed.

We have now found an industrially utilizable process for the microbial preparation of alcohols, aldehydes and carboxylic acids.

The invention relates to a process for preparing compounds of the formula I

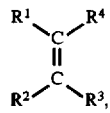

where $R^1$ is hydrogen, $C_{1-4}$-alkyl, $C_{2-4}$-alkenyl or unsubstituted or substituted aryl, $R^2$ is hydrogen, $C_{1-4}$-alkyl, $C_{2-4}$-alkenyl or unsubstituted or substituted aryl, or $R^1$ and $R^2$ form, together with the carbon atom to which they are bonded, a) a 6-membered ring which may contain 1 or 2 other double bonds and/or be substituted by 1, 2 or 3 halogen atoms, $C_{1-4}$-alkyl, $C_{2-4}$-alkenyl, $C_{1-4}$-acyl, $C_{1-4}$-alkoxy groups and/or 1 or 2 cyano, amino, $C_{1-4}$-alkylamino or di-$C_{1-4}$-alkylamino groups and/or one nitro group, and/or may be fused to another aromatic or heteroaromatic 6-membered ring to give a ring system which may be substituted by one to four $C_{1-4}$-alkoxy, $C_{1-4}$-alkyl, $C_{2-4}$-alkenyl, cyano, nitro, carboxyl, $C_{1-4}$-alkoxycarbonyl, amino, $C_{1-4}$-alkylamino, di-$C_{1-4}$-alkylamino and/or unsubstituted or substituted benzoyl group and/or one to four halogen atoms, or b) a heterocyclic 5-membered ring which contains 1, 2 or 3 heteroatoms and/or may contain another double bond and may be fused to another aromatic or heteroaromatic ring which may be substituted by one to four $C_{1-4}$-alkoxy, $C_{1-4}$-alkyl, $C_{2-4}$-alkenyl, cyano, nitro, carboxyl, $C_{1-4}$-alkoxycarbonyl, amino, $C_{1-4}$-alkylamino, di-$C_{1-4}$-alkylamino and/or an unsubstituted or substituted benzoyl group and/or one to four halogen atoms, $R^3$ is hydrogen or halogen, $C_{1-4}$-alkyl or $C_{2-4}$-alkenyl or unsubstituted or halogen-substituted aryloxy or benzoyl, and $R^4$ is —$CH_2OH$, —CHO or —COOH, which comprises the selective oxidation of a compound of the formula II

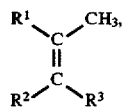

where $R^1$–$R^3$ have the abovementioned meanings, with the aid of a microorganism.

Alkyl radicals which may be mentioned for $R^1$ and $R^2$ are: methyl, ethyl, n-propyl, 1-methylethyl, butyl-, 1-methylpropyl, 2-methyl-propyl and 1,1-dimethylethyl. Preferred alkyl radicals are methyl, ethyl and propyl. Alkenyl radicals which may be mentioned are vinyl, 1-methylvinyl, cis-1-butenyl, trans-1-butenyl, cis-2-butenyl, trans-2-butenyl, 3-butenyl, 2-methyl-1-propenyl, 2-methyl-2-propenyl, 1-methyl-1-propenyl, 1-methyl-2-propenyl and 1-ethylvinyl. 2-Methyl-1-propenyl is preferred.

If $R^1$ is a substituted aryl group, this preferably carries $C_{1-4}$-alkyl, $C_{2-4}$-alkenyl and/or halogen radicals. Alkyl radicals which may be mentioned are: methyl, ethyl, n-propyl, 1-methylethyl, butyl, 1-methylpropyl, 2-methylpropyl and 1,1-dimethylethyl. Preferred alkyl radicals are methyl, ethyl and n-propyl. Alkenyl radicals which may be mentioned are vinyl, 1-methylvinyl, cis-1-butenyl, trans-1-butenyl, cis-2-butenyl, trans-2-butenyl, 3-butenyl, 2-methyl-1-propenyl, 2-methyl-2-propenyl, 1-methyl-1-propenyl, 1-methyl-2-propenyl and 1-ethylvinyl. 2-Methyl-1-propenyl is preferred. Halogen atoms which may be mentioned are fluorine, chlorine or bromine. Chlorine is preferred. The number of substituents on the aryl radical is normally 1–3. 1 or 2 radicals are preferred.

Aryl radicals which may be particularly mentioned for $R^1$ are phenyl and naphthyl.

If $R^2$ is a substituted aryl group, this preferably carries $C_{1-4}$-alkyl, $C_{2-4}$-alkenyl and/or halogen radicals. Alkyl radicals which may be mentioned are: methyl, ethyl, n-propyl, 1-methylethyl, butyl, 1-methylpropyl, 2-methylpropyl and 1,1-dimethylethyl. Preferred alkyl radicals are methyl, ethyl and propyl. Alkenyl radicals which may be mentioned are vinyl, 1-methylvinyl, cis-1-butenyl, trans-1-butenyl, cis-2-butenyl, trans-2-butenyl, 3-butenyl, 2-methyl-1-propenyl, 2-methyl-2-propenyl, 1-methyl-1-propenyl, 1-methyl-2-propenyl and 1-ethylvinyl. 2-Methyl-1-propenyl is preferred. Halogen atoms which may be mentioned are fluorine, chlorine or bromine. Chlorine is preferred. The number of substituents on the aryl radical is normally 1–3. 1 or 2 radicals are preferred.

Preferred radicals for $R^2$ are: phenyl, methyl, p-methoxyphenyl, 1,3-dioxanyl and 5,5-dimethyl-1,3-dioxanyl.

Aryl radicals which may be particularly mentioned for $R^2$ are phenyl and naphthyl.

If $R^1$ and $R^2$ form part of a ring or ring system, the following may be mentioned as preferred: phenyl, benzoyl, naphthyl, quinolinyl, isoquinolinyl, benzofuryl and benzoxazolyl.

Substituents which may be mentioned for these ring systems are:

Alkyl such as methyl, ethyl, propyl, 1-methylethyl, butyl, 1-methylpropyl, 2-methylpropyl, 1,1-dimethylethyl (especially methyl, ethyl and propyl); alkoxy such as methoxy, ethoxy, propyloxy, 1-methylethoxy, butyloxy, 1-methylpropyloxy, 2-methylpropyloxy, 1,1-dimethylethoxy (especially methoxy and 1-methylethoxy); alkenyl such as vinyl, 1-methylvinyl, cis-1-propenyl, trans-1-propenyl, 2-propenyl, cis-1-butenyl, trans-1-butenyl, cis-2-butenyl, trans-2-butenyl, 3-butenyl, 2-methyl-1-propenyl, 2-methyl-2-propenyl, 1-methyl-1-propenyl, 1-methyl-2-propenyl, 1-ethylvinyl (especially 2-methyl-1-propenyl); halogen such as fluorine, chlorine, bromine and iodine (especially fluorine and chlorine); alkoxycarbonyl such as methoxycarbonyl, ethoxycarbonyl, propyloxycarbonyl, 1-methylethoxycarbonyl, butyloxycarbonyl and 1,1-dimethylethoxycarbonyl (especially methoxycarbonyl and 1-methylethoxycarbonyl).

The number of substituents on the ring is normally 1–3, preferably 1 or 2.

$C_{1-4}$-Alkyl radicals on the amino group in the ring systems in $R^1$ and $R^2$ which may be mentioned are: ethyl, propyl, 1-methylethyl, butyl, 1-methylpropyl, 2-methylpropyl, 1,1-dimethylethyl and, in particular, methyl.

The following radicals may be specifically mentioned for $R^3$: methyl, ethyl, n-propyl, 1-methylethyl, butyl, 1-methylpropyl, 2-methylpropyl, 1,1-dimethylethyl, vinyl, 1-methylvinyl, cis-1-propenyl, trans-1-propenyl, 2-propenyl, cis-1-butenyl, trans-1-butenyl, cis-2-butenyl, trans-2-butenyl, 3-butenyl, 2-methyl-1-propenyl, 2-methyl-2-propenyl, 1-methyl-1-propenyl, 1-methyl-2-propenyl, 1-ethylvinyl, fluorine, chlorine and bromine. Preferred for $R^3$ are: methyl, ethyl, n-propyl and 2-methyl-1-propenyl.

The novel process is particularly suitable for preparing alcohols and, in particular, carboxylic acids.

Bacteria which carry out the oxidation according to the invention can be isolated and identified by screening by the method of Drews (Mikrobiologisches Praktikum, 3rd Edition, Springer Verlag, pages 47–48, 1976) from soil samples and collections of strains.

Examples of bacteria suitable for the reaction according to the invention are those listed in the past under the genus names Arthrobacter, Bacillus, Brevibacterium, Corynebacterium, Caseobacter, Gordona, Micrococcus, Mycobacterium, Nocardia, Planococcus, Proactinomyces, Rhodococcus, Staphylococcus, Serratia and Tsukamurella and specifically under the genus and species names Arthrobacter sp., *Bacillus rubropertinctus, Bacillus mycoides roseus, Bacillus rubricus, Corynebacterium rubrum, Gordona lentifragmenta, Gordona rubropertinctus, Gordona rubra, Micrococcus roseus, Micrococcus roseus roseofulvus, Micrococcus tetragenus ruber, Micrococcus rubens, Micrococcus flavoroseus, Micrococcus corallinus, Micrococcus agilis, Mycobacterium rubropertinctus, Nocardia corallina, Nocardia rubra, Nocardia sp., Nocardia salmonicolor, Nocardia pellegrino, Proactinomyces ruber, Proactinomyces rubropertinctus, Rhodococcus ruber, Rhodococcus rhodochrous, Rhodococcus erythropolis, Rhodococcus rubra, Rhodococcus rubrus,* Rhodococcus sp., *Rhodococcus roseus, Rhodococcus lentifragmentus, Rhodococcus agilis, Serratia rubropertincta* and *Staphylococcus roseus.*

The large number of bacteria suitable for the reaction reflects the many changes in the past in the taxonomy of the families Mycobacteriaceae, Nocardiaceae and Micrococcaceae with their genera Corynebacterium, Gordona, Mycobacterium, Nocardia, Rhodococcus, Tsukamurella, Micrococcus, Staphylococcus and Planococcus.

Details are to be found in The Procaryotes (ed. Balows A. et al.) 1992, Vol. II., Bergey's Manual of Determinative Bacteriology, Eighth Edition (ed. Cowan S. et al.) 1974, Bergey's Manual of Systematic Bacteriology (ed. Seneath P.H.A. et al.) 1986, Vol. II. ATCC-Catalogue of Bacteria & Bacteriophages 17th Edition 1989, Kocur M. et al., Int. J. Syst. Bacteriol. 20, (1970) 233–240, and Tsukamura M. et al. Int. J. Syst. Bacteriol. 25, (1975) 377–382 and J. Gen. Microbiol. 68, (1971) 15–26, 80, (1974) 553–555 and 125, (1981) 205–208.

The taxonomic position of the genera mentioned has undergone great changes in recent years and is still in a state of flux because incorrect genus and species names are being corrected and existing strains are being assigned to new genera. There are close relationships within these genera and species. Bacteria which carry out the reaction according to the invention are highly likely to be found in the above-mentioned genera and species.

The following strains are particularly suitable for the methyl group oxidation:

*Rhodococcus ruber (Nocardia pellegrino)* DSM 43232, *Rhodococcus ruber (Rhodococcus rubrus,* Nocardia sp.) DSM 43250, *Rhodococcus ruber (Rhodococcus rubrus,* Nocardia sp.) DSM 43251, *Rhodococcus ruber (Rhodococcus rubrus,* Nocardia sp.) DSM 43252, *Rhodococcus ruber (Rhodococcus rubrus,* Nocardia sp.) DSM 43335, *Rhodococcus ruber (Rhodococcus rubrus,* Nocardia sp.) DSM 43338, *Rhodococcus ruber (Nocardia pellegrino)* IMET 7308, *Rhodococcus ruber* IMET 7337, *Rhodococcus ruber (Rhodococcus lentifragmentus, Gordona lentifragmenta)* IMET 7437 and *Rhodococcus ruber (Gordona lentifragmenta)* IMET 7477, *Rhodococcus ruber (Nocardia rubra)* LMG 5366, *Micrococcus roseus (Micrococcus roseus roseofulvus, Micrococcus tetragenus ruber)* ATCC 178, *Micrococcus roseus (Micrococcus rubens, Micrococcus roseus roseofulvus, Micrococcus tetragenus ruber)* ATCC 186, *Micrococcus roseus (Rhodococcus roseus)* ATCC 516, *Micrococcus roseus (Rhodococcus ruber)* ATCC 534 and *Micrococcus roseus* ATCC 9815.

The former names of these strains are shown in parentheses.

The strain which is very particularly suitable for the oxidation is Rhodococcus ruber DSM 8316 and mutants derived therefrom. This strain is charactereized by the data shown in the Annex.

Rhodococcus ruber DSM 8316 is an isolate from soil samples.

A deposit of Rhodococcus ruber DSM 8316 has been made under the accession number given by the International Depositary Authority of DSM 8316. The name of the depository is DSM Deutsche Sammlung von Mikroorganismen und Zellkulturen GmbH, located at Mascheroder Web 1B, D-3300 Braunschweig.

The methyl group must be in the benzylic or allylic position in order to be oxidizable to the corresponding alcohol, aldehyde or carboxylic acid. If the precursor contains several benzylic or allylic methyl groups, as a rule only one methyl group is oxidized selectively. In rare cases (<5%), another methyl group is oxidized.

Since the precursors are transformed in the sequence alcohol, aldehyde, carboxylic acid, and serve as source of carbon and energy for the wild-type strains mentioned, it is expedient, in order to obtain the desired products, to use block mutants of the bacteria mentioned, which carry out the oxidation only to the alcohol, or only to the aldehyde or only to the carboxylic acid.

Known microbiological techniques can be used to produce such block mutants. All conventional methods can be used to induce mutations, such as the use of mutagenic substances, eg. nitrosoguanidines, ethyl methanesulfonate, sodium nitrite, or the action of electromagnetic radiation such as UV, gamma or X-rays. An appropriate method for preparing N-methyl-N'-nitro-N-nitrosoguanidine is to be found in Biochem. Biophys. Res. Commun. 18, (1965) 788. It is also possible to use transposable genetic elements for the mutagenesis.

It is possible, for example, to make use of the property of no longer growing on the products of the oxidation as sole carbon source in order to isolate the mutants.

The use of such block mutants is a preferred embodiment of the invention.

The process according to the invention for oxidizing benzylic and allylic methyl groups on fused and unfused aromatic and heteroaromatic compounds, and aliphatic compounds, is expediently carried out by cultivating the bacteria or their mutants in a suitable medium with a suitable source of carbon and energy in the presence of the appropriate precursors, or adding the precursors to the nutrient solution after cultivation for 24 to 72 h. Precursors of low solubility are expediently added as emulsion with a commercial emulsifier (eg. Tween® 80) to the nutrient medium.

The fermentation is carried out continuously or batchwise for 1-14 days.

As a rule, the oxidation is carried out with active bacteria, but it is also possible with dormant bacteria, although at a considerably lower rate.

Suitable nutrient media contain carbon sources, nitrogen sources, inorganic salts and, where appropriate, small amounts of trace elements and vitamins. Nitrogen sources which can be used are inorganic or organic nitrogen compounds or materials which contain these compounds. Examples are ammonium salts, nitrates, corn steep liquor, brewer's yeast autolyzate, soybean meal, wheat gluten, yeast extract, yeast, urea and potato protein.

Examples of carbon sources which can be used are sugars such as glucose, polyols such as glycerol or fats such as soybean oil.

Examples of inorganic salts are the salts of calcium, magnesium, manganese, potassium, zinc, copper and iron. The phosphate ion may be mentioned in particular as anion of the salts.

Growth factors are added where appropriate to the nutrient medium, eg. biotin, riboflavin and/or other vitamins.

The mixing ratio of said nutrients depends on the mode of fermentation and is established in the individual case.

Generally suitable for carrying out the process according to the invention are precursor concentrations of about 1–100 g/l, preferably about 3–50 g/l, particularly preferably about 5–20 g/l.

The cultivation conditions are established to achieve the best possible yields. Preferred cultivation temperatures are from 15° C. to 40° C. Particularly advantageous temperatures are from 25° C. to 35° C. The pH is preferably maintained in a range from 3 to 9. pH values from 5 to 8 are particularly advantageous. An incubation time of from 15 to 120 hours is generally sufficient. During this time, the maximum amount of the required product accumulates in the medium.

The extent of conversion can easily be followed and monitored by taking a sample and investigating it by, for example, gas chromatography or HPLC analysis. The products can be isolated and purified from the culture liquid by conventional methods. Expediently, the solid biomass is separated from the nutrient medium, the product is extracted with, for example, an organic solvent, where appropriate after acidification of the medium, and the product is isolated from the extracted phase. Column chromatography is also expedient for the workup.

EXAMPLES

The following examples illustrate the invention.

Two media were used for the examples:

| Medium A (complex medium) | | |
|---|---|---|
| 10.0 | g/l | Yeast extract |
| 20.0 | g/l | Glucose |
| 0.5 | g/l | Magnesium sulfate 7-hydrate |
| 1.5 | g/l | Potassium dihydrogen phosphate |
| 3.6 | g/l | Dipotassium hydrogen phosphate |
| 2 | mg/l | Iron (II) sulfate 1-hydrate |
| 5 | mg/l | ®Titriplex III |
| 100 | µg/l | Zinc (II) sulfate 4-hydrate |
| 300 | µg/l | Boric acid |
| 200 | µg/l | Cobalt (II) chloride 6-hydrate |
| 10 | µg/l | Copper (II) chloride 2-hydrate |
| 20 | µg/l | Nickel (II) chloride 6-hydrate |
| 30 | µg/l | Sodium molybdate 2-hydrate |

| Medium B (minimal medium) | | |
|---|---|---|
| 5.0 | g/l | Glucose |
| 2.0 | g/l | Potassium dihydrogen phosphate |
| 0.5 | g/l | Magnesium sulfate 7-hydrate |
| 0.2 | g/l | Calcium chloride 7-hydrate |
| 2.0 | g/l | Sodium chloride |
| 0.5 | g/l | Urea |
| 2 | mg/l | Iron (II) sulfate 1-hydrate |
| 5 | mg/l | ®Titriplex III |
| 100 | µg/l | Zinc (II) sulfate 4-hydrate |
| 300 | µg/l | Boric acid |
| 200 | µg/l | Cobalt (II) chloride 6-hydrate |
| 10 | µg/l | Copper (II) chloride 2-hydrate |
| 20 | µg/l | Nickel (II) chloride 6-hydrate |
| 30 | µg/l | Sodium molybdate 2-hydrate |
| 2 | µg/l | Biotin |
| 2 | µg/l | Folic acid |
| 200 | µg/l | p-Aminobenzoic acid |

-continued

| 200 | μg/l | Riboflavin |
|---|---|---|
| 400 | μg/l | Ca pantothenate |
| 1400 | μg/l | Nicotinic acid |
| 400 | μg/l | Pyridoxine/HCl |
| 2000 | μg/l | Meso-inositol |
| 400 | μg/l | Thiamine/HCl |

The pH of the medium was adjusted to 6.8 with 5N sodium hydroxide or potassium hydroxide solution. Glucose and phosphate were each autoclaved separately at 121° C. for 20 min. Urea, vitamins and the appropriate precursors were sterilized by filtration. Precursors which could not be filtered were assumed to be autosterile. The remaining medium was autoclaved at 121° C. for 20 min.

Example 1

In each case 20 ml of the appropriate medium were introudced into sterile 100 ml Erlenmeyer flasks, which were then closed with a sterile cotton plug. The culture broth was inoculated in each case with a loop of DSM 8316. The precursors listed in Table 1 were introduced at a concentration of 5 g/l in medium B. The flasks were incubated at 28° C. while agitating at 150 revolutions per min (rpm) for three to ten days.

The culture broths (see Tables 1 and 3) were then worked up and analysed (cf. Example 4). The products were identified by GC, GC/MS and $^1$H—NMR. Authentic chemically synthesized samples were used as reference.

TABLE 1

Biotransformation with DSM 8316 - precursors and analysed products

| Precursor | Product |
|---|---|
| 4-Isopropyltoluene | 4-Isopropylbenzoic acid |
| 2-(4-Methylphenoxy)propane | 4-Isopropoxybenzoic acid |
| 4-Methylanisole | 4-Methoxybenzoic acid |
| 4-Methylacetophenone | 4-Acetylbenzoic acid |
| 4-Cyanotoluene | 4-Cyanobenzoic acid |
| 4-Chlorotoluene | 4-Chlorobenzoic acid |
| 4-Vinyltoluene | 4-Vinylbenzoic acid |
| 4-Nitrotoluene | 4-Nitrobenzoic acid |
| 2,3-Dimethyl-4-nitrobenzene | 2-Methyl-4-nitrobenzoic acid |
| 2-Chloro-4-methylnitrobenzene | 2-Chloro-4-nitrobenzoic acid |
| 2,4-Dimethylbenzophenone | 2-Methyl-4-benzoylbenzoic acid |
| 2-Methylnaphthalene | 2-Naphthoic acid |
| 2,6-Dimethylnaphthalene | 6-Methyl-2-naphthoic acid |
| 6-Methylquinoline | 6-Quinolinecarboxylic acid |
| 2,6-Dimethylquinoline | 2-Methyl-6-quinolinecarboxylic acid |
| 6-Methylisoquinoline | 6-Isoquinolinecarboxylic acid |
| p-Xylene | p-Toluic acid |
| 4-tert-Butyltoluene | 4-tert-Butylbenzoic acid |
| 2-Methylindole | 2-Indolylcarboxylic acid |
| 2-Methylbenzoxazole | 2-Benzoxazolecarboxylic acid |
| 2-Methylbenzofuran | Benzofuran-2-carboxylic acid |
| 4-(Methyl-1-propenyl)anisole | 4-Methoxy-α-methylcinnamic acid |
| Limonene | Perillic acid |
| 2-(2-Methyl-1-propenyl)-5,5-dimethyl-1,3-dioxane | 3-Formyl-2-methyl-2-propenoic acid 2,2-dimethylpropylene acetal |

3-Formyl-2-methyl-2-propenoic acid 2,2-dimethylpropylene acetal (formula III) is a novel compound which is very suitable for preparing polyenes and carotenoids.

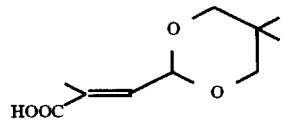

Example 2

The microorganisms listed in Table 2 were cultured in medium A as in Example 1. In each case 5 g/l of the precursors mentioned in Table 3 were added to the medium. The products detected as in Example 1 are likewise to be found in Table 3.

TABLE 2

| Microorganisms | |
|---|---|
| Rhodococcus ruber | DSM 43250, DSM 43251, DSM 43252, DSM 43232, DSM 43335 and DSM 43338 |
| Rhodococcus ruber | IMET 7308, IMET 7337, IMET 7437 and IMET 7477 |
| Rhodococcus ruber | LMG S366 |
| Micrococcus roseus | ATCC 178, ATCC 186, ATCC 516, ATCC 534 and ATCC 9815 |

TABLE 3

Biotransformation with microorganisms listed in Table 2 - precursors and analysed products

| Precursor | Product |
|---|---|
| 2-(4-Methylphenoxy)propane | 4-Isopropoxybenzoic acid |
| 4-Cyanotoluene | 4-Cyanobenzoic acid |
| 4-Chlorotoluene | 4-Chlorobenzoic acid |
| 2-Methylbenzofuran | Benzofuran-2-carboxylic acid |
| Limonene | Perillic acid |
| 2-(2-Methyl-1-propenyl)-5,5-dimethyl-1,3-dioxane | 3-Formyl-2-methyl-2-propenoic acid 2,2-dimethylpropylene acetal |

Example 3

DSM 8316 was cultured in 100 ml of medium A in a 500 ml Erlenmeyer flask as in Example 1. 5 g/l 2-(4-methylphenoxy)propane were added to the medium. A further 2.5 g/l precursor were added after incubation for 24 h and 48 h. The culture broth was worked up afer incubation for 120 h. The products identified besides 4-isopropoxybenzoic acid as main product were small amounts of 4-isopropoxybenzaldehyde and 4-isopropoxybenzyl alcohol. The products were identified as described in Example 1.

Example 4 a) Preparation of block mutants

Starting from DSM 8316, mutants were selected as described in Biochem. Biophys. Res. Commun. 18 (1965) 788. For this purpose, DSM 8316 was cultivated in 20 ml of medium B overnight (30° C., 120 rpm, 16 h). The cells were then harvested (centrifugation: 10 min, 4° C., 5,000 g) and washed twice with 100 mM tris/HCl buffer (pH 7.2). The cells obtained in this way were adjusted with the buffer to an optical density at 600 nm of 0.75. 0.5 ml of this cell suspension was mutagenized by adding 1% N-methyl-N'-nitro-N-nitrosoguanidine in DMF in the presence of 100 mM tris/maleic acid buffer (pH 6.0) (room temperature, 30 min, 120 rpm). The volume of the mixture was 5 ml.

After mutagenesis, the cells were washed twice with 100 mM tris/HCl buffer (pH 7.2), and serial 10-fold dilutions down to $10^{-7}$ were plated out on medium B agar (=medium B+20 g/l agar) (=master plates). After incubation at RT for 4 days, for selection the resulting colonies were replica plated onto medium B agar plates (=replica plates) without glucose but with the appropriate precursors and products as sole carbon source (0.5 g/l), as described in Microbiology, Third Edition, Harper International Edition, 1980. Comparison of the replica plates with the master plates permitted block mutants to be identified. The selection criterion for the block mutants were lack of growth on precursors and products as sole carbon source.

One of the block mutants obtained in this way (=4a1) was cultivated in 100 ml of medium A in the presence of 5 g/l 2-(4-methylphenoxy)propane as described in Example 1. After incubation for 7 days, 1,000 µl of fermentation broth were removed and, after addition of 100 µl of 1N HCl and 500 µl of MTB (methyl tert-butyl ether), vigorously mixed for 1 min. 400 µl of the organic phase were cautiously removed and concentrated under reduced pressure.

The residue was taken up in 100 µl of MTB and transferred quantitatively into a sample vial for gas chromatography. 50 µl of N-methyl-N-trimethylsilyltrifluoroacetamide were added to the sample. The only product detected by gas chromatography was 4-isopropoxybenzoic acid. This was confirmed by GC/MS, $^1$H—NMR and comparison with an authentic reference sample.

Repetition of the incubation with another block mutant (4a2 or 4a3) leads to the detection of 4-isopropoxybenzyl alcohol as sole product with mutant 4a2 and of 4-isopropoxybenzaldehyde as sole product with mutant 4a3.

Example 5 b) Preparation of 4-isopropoxybenzoic acid 100 ml of medium A were inoculated with a loop of block mutant 4a1 and incubated for 48 h. 50 ml of this culture were used in inoculate a laboratory fermenter containing 1 l of medium A and 5 g of 2-(4-methylphenoxy)propane as precursor. A further 2.5 g of 2-(4-methylphenoxy)propane were added after incubation for 24 h and 48 h. Fermentation was stopped after incubation for 168 h. First the biomass was removed by centrifugation (30 min, 4° C., 10,000 g) and then the remaining cells were removed by filtration. The culture broth was subsequently adjusted to pH 1.0 with concentrated $H_2SO_4$ and extracted twice with 250 ml of MTB each time. The organic phase was removed and concentrated in a rotary evaporator. It was possible to isolate 7.1 g of 4-isopropoxybenzoic acid in chemically pure form. This corresponds to a yield of about 60%.

Example 6 c) Preparation of 4-isopropoxybenzyl alcohol 100 ml of medium A were inoculated with a loop of block mutant 4a2 and incubated at 30° C. and 120 rpm for 48 h. 50 ml of this culture were used to inoculate a 1 l laboratory fermenter containing medium A and 5 g of 2-(4-methylphenoxy)propane as precursor. The fermentation was stopped after incubation for 168 h. Firstly the biomass was removed by centrifugation (30 min, 4° C., 10,000×g) and then the remaining cells were removed by filtration. The culture broth was subsequently extracted twice with 250 ml of MTB each time. The organic phase was removed (MTB phase 1). After adding concentrated $H_2SO_4$ to pH 1.0, two further extractions with 250 ml of MTB each time were carried out. The organic phase was removed again (MTB phase 2). The organic phases were combined, concentrated in a rotary evaporator and analysed (see Example 1). It was possible to isolate 942 mg of 4-isopropoxybenzyl alcohol as sole product in chemically pure form. This corresponds to a yield of about 20%.

Description of the microorganism DSM 8316:

The strain DSM 8316 was identified by the DSM (Deutsche Sammlung von Mikroorganismen und Zellkulturen GmbH, Braunschweig) as *Rhodococcus ruber*. The determination record is as follows:

1. Color type: 70 pastel orange to pure orange
2. Peptidoglycan: meso-diaminopimelic acid
3. Mycolic acids: chain length $C_{30}$–$C_{50}$
4. Fatty acid pattern: unbranched saturated and unsaturated fatty acids plus tuberculostearic acid. This fatty acid pattern is diagnostic for rhodococci and related organisms.
5. Menaquinones: MK-8 ($H_2$)
6. Test on 35 other substrates

| Name | Total P | Willcox P | Tax distance | Std. error |
|---|---|---|---|---|
| Rh. ruber | 310E–0014 | 78.05% | 0.495860003 | –4.451097 |
| Rh. marinonascens 43752T | 7.5E–0015 | 19.69% | 0.442831797 | 1.096741 |
| Rh. rhodochrous | 4.7E–0016 | 1.22% | 0.509506764 | –4.942624 |
| Rh. coprophilus | 4.0E–0016 | 1.03% | 0.477056451 | –2.850872 |

Test results:

| | | | | | | | | |
|---|---|---|---|---|---|---|---|---|
| nag | 1 | – | gal | 40 | – | gct | 1 | – | got | 20 | – |
| gat | 1 | – | rha | 60 | – | rib | 1 | – | suc | 40 | – |
| tur | 1 | – | cap | 1 | – | ara | 99 | + | ino | 20 | – |
| cit | 80 | + | o2V | 1 | – | o2g | 20 | + | pim | 99 | – |
| sat | 80 | – | ala | 20 | – | a4b | 80 | – | asp | 6 | – |
| leu | 80 | – | pro | 1 | – | ser | 1 | – | val | 80 | – |
| put | 99 | – | tyr | 1 | – | ata | 99 | – | ben | 80 | – |
| o3b | 99 | + | o4b | 99 | + | phe | 1 | + | qui | 99 | + |
| cxy | 1 | – | cch | 99 | + | cdp | 99 | + | | | |

Number of tests: 35/35
Calculation function: 99/1
Cluster of 16 tested strains

DSM 8316 is *Rhodococcus ruber* strain with a Willcox probability of 90%.

We claim:

1. A process for preparing compounds of the formula I

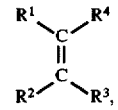

where
$R^1$ is hydrogen, $C_{1-4}$-alkyl, $C_{2-4}$-alkenyl or unsubstituted or substituted aryl, $R^2$ is hydrogen, $C_{1-4}$-alkyl, $C_{2-4}$-alkenyl or unsubstituted or substituted aryl, or $R^1$ and $R^2$ form, together with the carbon atom to which they are bonded, a) a ring or ring system selected from the group consisting of phenyl, benzoyl, naphthyl, quinolinyl, isoquinolinyl, benzofuryl and benzoxazolyl which may be substituted by halogen, alkyl, alkenyl, alkoxycarbonyl or b) a heterocyclic 5-membered ring which contains 1, 2 or 3 heteroatoms and or may contain another double bond and may be fused to another aromatic or heteroaromatic ring which may be substituted by one to four $C_{1-4}$-alkoxy, $C_{1-4}$-alkyl, $C_{2-4}$-alkenyl, cyano, nitro, carboxyl, $C_{1-4}$-alkoxycarbonyl, amino, $C_{1-4}$-alkylamino, di-$C_{1-4}$- alkylamino and/or an unsubstituted or substituted benzoyl group and/or one to four halogen atoms, R³ is hydrogen or halogen, $C_{1-4}$-alkyl or $C_{2-4}$-alkenyl or unsubstituted or halogen-substituted aryloxy or benzoyl, and which comprises the selective oxidation of a compound of the formula II

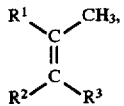

where $R^1$–$R^3$ have the abovementioned meanings, with the aid of a bacterium of the genus Arthrobacter, Bacillus, Brevibacterium, Corynebacterium, Caseobacter, Gordona, Micrococcus, Mycobacterium, Nocardia, Planococcus, Proactinomyces, Rhodococcus, Staphylococcus, Serratia or Tsukamurella.

2. A process as defined in claim 1, wherein the bacterium used is *Micrococcus roseus*.

3. A process as defined in claim 1, wherein the bacterium used is *Rhodococcus ruber*.

4. A process as defined in claim 1, wherein the bacterium used is *Rhodococcus ruber* DSM 8316.

5. 3-Formyl-2-methyl-2-propenoic acid 2,2-dimethylpropylene acetal.

6. A process as defined in claim 1, wherein the bacterium used is a block mutant selected from *Rhodococcus ruber* DSM 8316.

7. A process as defined in claim 1, wherein the bacterium used is a block mutant selected from *Micrococcus roseus*.

8. A process as defined in claim 1, wherein the bacterium used is a block mutant selected from *Rhodococcus ruber*.

* * * * *